United States Patent [19]

Gavezotti et al.

[11] Patent Number: 4,681,693

[45] Date of Patent: Jul. 21, 1987

[54] STABILIZERS WITH ARYLPHOSPHINIC STRUCTURE FOR PERFLUORO-POLYETHER OILS AND GREASES

[75] Inventors: Piero Gavezotti, Milan; Ezio Strepparola, Treviglio, both of Italy

[73] Assignee: Ausimont S.p.A., Milan, Italy

[21] Appl. No.: 854,786

[22] Filed: Apr. 23, 1986

[30] Foreign Application Priority Data

Apr. 24, 1986 [IT] Italy ................. 20475 A/85

[51] Int. Cl.$^4$ .......................................... C10M 137/14
[52] U.S. Cl. ..................... 252/49.9; 568/16; 568/17
[58] Field of Search ................ 252/49.9; 568/16, 17

[56] References Cited

U.S. PATENT DOCUMENTS

| | | | |
|---|---|---|---|
| 3,393,151 | 7/1968 | Dolle et al. | 568/16 |
| 3,483,129 | 12/1969 | Dolle et al. | 252/49.9 |
| 4,431,556 | 2/1984 | Christian et al. | 252/49.9 |
| 4,438,007 | 3/1984 | Snyder, Jr. et al. | 252/49.9 |
| 4,454,349 | 6/1984 | Lamborski et al. | 252/49.9 |

*Primary Examiner*—Jacqueline V. Howard
*Attorney, Agent, or Firm*—Stevens, Davis, Miller & Mosher

[57] ABSTRACT

New products having the structure of arylphosphines or of derivatives of arylphosphines with an oxygen or sulphur atom directly bonded to the phosphorus atom, containing perfluoroalkylether chains, characterized in that such chains are bonded to the benzene ring through a non-perfluorinated bridge, and are obtained by a process substantially decreasing their production costs, and suitable to be used as stabilizers of perfluoropolyether oils and greases to prevent their degradation in the presence of metals, and the corrosion of the same metals, such as, e.g., Al, Ti, V, or their alloys, when operating in oxidizing and high-temperature environments.

10 Claims, No Drawings

STABILIZERS WITH ARYLPHOSPHINIC STRUCTURE FOR PERFLUORO-POLYETHER OILS AND GREASES

BACKGROUND OF THE INVENTION

1. Field of the Invention

The present invention relates to new stabilizer products for lubricant oils and greases having perfluoropolyether structure. The so stabilized lubricants are resistant to degradation and do not corrode the metals, such as, e.g., Al, Ti, V, or their alloys, or steels at temperatures comprised within the range of from $-50°$ C. to $>+300°$ C., under oxidizing atmosphere and when the metal or alloy and the lubricant, either as oil or as grease, are in contact with each other.

More particularly, the invention relates to stabilizers on the basis of arylphosphines or of derivatives of arylphosphines, possibly having an oxygen or sulphur atom directly bonded to the phosphorus atom, containing at least one perfluoroether chain in their molecule. Further object of the invention is to provide a process which can be easily implemented on industrial scale and allowing the above said stabilizers to be produced with considerable reductions in production costs.

2. Description of the Prior Art

It is known that the use of fluids having polyperfluoropolyether structure at high temperature under an oxidizing atmosphere causes with time, generally within a time period of about twenty hours, a progressive degradation of the fluid, when this is in contact with metals or alloys. The degradation depends both on the conditions under which the fluid is used, and on its chemical structure.

For example, perfluoropolyether fluids marketed under the trade name Fomblin Z ® result less stable than the corresponding Fomblin Y ® or Krytox ® products, when they are used under an oxidizing atmosphere at high temperature, e.g., at temperatures comprised within the range of from 200° C. to 300° C., in the presence of titanium or of titanium-based metal alloys.

From the prior art perfluoroarylphosphines, disclosed in U.S. Pat. No. 3,393,151 and 3,499,041, and used as corrosion and degradation inhibitors in perfluoropolyether fluids, are known. They are characterized by having three perfluorinated benzene rings bonded to the phosphorus atom or to the phosphinoxido group (U.S. Pat. No. 3,393,151), or the perfluorinated benzene rings can be differently substituted with always completely fluorinated groups of the type of: $C_nF_{2n+1}$, $C_6F_5$, $C_6F_5O$, $C_nF_{2n+1}$-$C_6F_4$, $C_nF_{2n+1}$-$C_6F_4O$, with n being comprised between 1 and 8.

Although such products perform their action as inhibitors of metal corrosion and of perfluoropolyether degradation, as hereinabove mentioned, they are however poorly soluble in perfluoropolyethers at low temperatures, and moreover some of these compounds result volatile at high temperature.

Furthermore, in U.S. Pat. No. 3,567,803 are described stabilizers of the class of phosphinates having the following structural formulae:

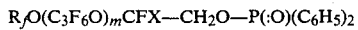

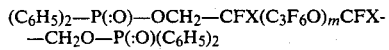

wherein $R_f$ is a perfluoroalkyl chain containing from 1 to 6 carbon atoms, m is an integer comprised between 3 and 50, X is —f or —$CF_3$. Such compounds are used as inhibitors of high temperature degradation and corrosion in hydraulic and lubricant fluids having perfluoropolyether structure. Phosphinates of this type, however, do not show good stability characteristics, and moreover have poor low-temperature solubility in the fluids to be stabilized.

Moreover, the amount of phosphinate to be added to perfluoropolyether, according to the said patent, must be quite high, of the order of 5–10% by weight. Amounts of stabilizer as high as these, besides impairing the fluodynamic characteristics of the perfluoropolyether fluid, render still more critical the low-temperature solubility of these additives in perfluoropolyethers, and this causes considerable storage problems, due to the precipitation of the stabilizer. Furthermore, these stabilizers, even when they are stored separately, must be kept under conditions as anhydrous as possible, because they are very sensible to the hydrolysis.

All these drawbacks limit the application thereof as stabilizers of perfluoropolyethers.

Arylphosphines, not necessarily completely fluorinated, are also known from U.S. Pat. No. 4,011,267, to be used as stabilizers for the above mentioned applications, having formulae of

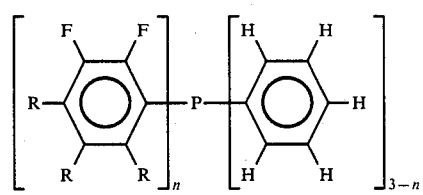

type, wherein one R radical is a perfluoroalkylether of general formula

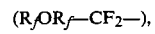

the other two R radicals are F and n ranges from 1 to 3.

The group $R_fOR_f$ can be of the type

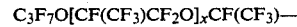

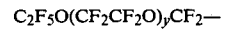

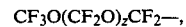

wherein x, y, z are zero or an integer ranging from 1 to 20, preferably from 1 to 4 included.

These stabilizers are prepared by starting from dibromotetrafluorobenzene, which is reacted with a Grignard compound, e.g., ethylmagnesium bromide; a treatment is then carried out with a cuprous halide. The organocuprous compound so obtained is reacted with a perfluoroacyl halide

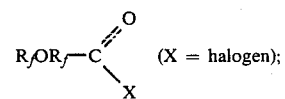

a ketone is so obtained, which is reacted with $SF_4$ in the presence of anhydrous HF.

The so functionalized bromobenzene is treated with butyllithium and subsequently with PCl₃ or dichlorophenyl phosphine or chlorodiphenylphoshine, to yield the products according to the patent.

Such a preparation method is not much interesting from a practical viewpoint, in that it requires very complex reactions, which cannot be proposed for a full-scale application. By this method, products are obtained in very small amounts at of very high cost.

Arylphosphines, disclosed in U.S. Pat. No. 4,454,349, are moreover known, of general formula:

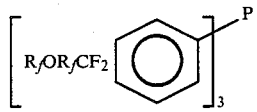

wherein the group $R_fOR_f$, similarly to as in the above mentioned patent, can be of the type $C_3F_7O[CF(CF_3)CF_2O]_xCF(CF_3)$—

$C_2F_5O(CF_2CF_2O)_yCF_2$—

$CF_3O(CF_2O)_zCF_2$—, and the indexes x, y, z are 0 or an integer of value of from 1 to 20, preferably of from 1 to 4 included.

Such products are obtained by reacting a dibromobenzene with butyllithium, the compound obtained is then reacted with a perfluoropolyether, having an ester as the end group, to obtain the ketone; the carbonyl group is then fluorinated by SF₄ and HF. The so-obtained product is treated with butyllithium and then with PCl₃ to obtain the triarylphosphinic compounds.

Such arylphosphines have the same stabilizing properties as of those disclosed in prior U.S. Pat. No. 4,011,267, but they are obtained by a more simplified process, and starting from cheaper precursors, that considerably reduces the production costs, even if these remain however very high.

Also this process results not suitable to a full-scale passage, in that it contains, as critical and essential step, the reaction of fluorination of C=O group by SF₄ and HF.

Such a fluorination by SF₄ and HF involves problems both as for the equipment required, and as for the control of the fluorination reaction, due to the following reasons:

(1) low reaction rates;
(2) use of high pressure and temperature values, respectively of the order of 70-80 atm, and T=150°-170° C.;
(3) dangerousness of SF₄ and HF reactants under the indicated temperature and pressure conditions;
(4) need for special materials for plant construction;
(5) extreme difficulty in monitoring the fluorination proceeding, due to the physical-chemical characteristics of the reactants and by-products (SF₄ and SOF₂) used as the test compounds for the check of the proceeding of the reaction;

this latter drawback enormously reduces the potentiality of the reactor, and leads to not quantitative reactions, wich consequent need to use sophisticated rectifying equipment to separate the starting product from the end product, which have very close physical-chemical characteristics.

THE PRESENT INVENTION

New products have been now surprisingly found, with stabilizing characteristics comparable to those of the products disclosed in U.S. Pat. No. 4,011,267 and 4,454,349, but which can be obtained by a synthesis which eliminates the critical step of fluorination by SF₄ and HF, reaction considered as essential to obtain products with high stability characteristics for the applications as described.

The synthesis of these new products can be easily carried out on industrial scale, gives high yields in stabilizers and results much less burdensome from the financial viewpoint, allowing low-cost stabilizer products for perfluoropolyether oils and greases, for use in the presence of metals or alloys at high temperatures and under oxidizing atmosphere, to be offered on the market.

The object of the present invention are hence new products having the structure of arylphosphines or derivatives thereof, with an oxygen or sulphur atom directly bonded to the phosphorus atom, containing at least one perfluoroether chain as a substituent on the benzene rings, and suitable to be used as stabilizers of perfluoropolyether oils and greases, so as to prevent the degradation thereof and the corrosion of metals, such as, e.g., Al, Ti, V or their alloys, or steels when the lubricants are used in an oxidizer environment, at high temperature, in the presence of the above said metals or alloys.

The new products being the object of the invention are selected from the following classes of compounds having the general formulae:

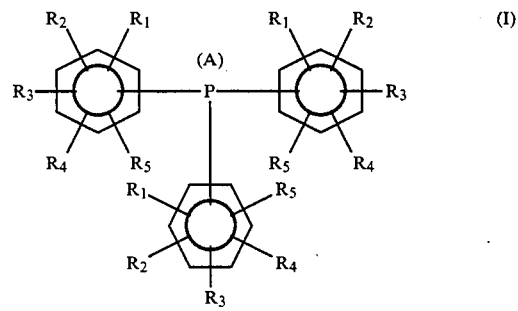

wherein
A, when is present, can be either oxygen or sulphur;
$R_1, R_2, R_3, R_4, R_5$, equal to, or different from each other, can be —H, —F, —CF₃, —B—$R_{f1}$, with the constraint that at least one of the various $R_1$-$R_5$ groups on at least one of benzene rings is a —B—$R_{f1}$ radical, wherein $R_{f1}$ is:

(a) Z—CF₂O(C₃F₆O)$_m$(CFXO)$_n$—CFY—, wherein
X=—F, —CF₃;
Y=—F, —CF₃;
Z=—F, —CF₃ or —CF₂—CF₃; in this second case n=0 and Y=—CF₃;
m and n are integers, with m being comprised between 1 and 30 and n being comprised between 0 and 10, and the molecular weight of $R_{f1}$ is comprised withn the range of from 135 to 6500 and (C₃F₆O) and (CFXO) units are randomly distributed along the chain;
said chains are obtained according to UK Pat. No. 1,104,482;

(b) Z—(CF₂CF₂CW₂O)$_p$— wherein z has the meaning described above, W is H or F and p is an integer from 1 to 30; said chains are obtained according to EP Appln. 148,482;

(c) D—(CF$_2$CF$_2$O)$_q$—
wherein D is —CF$_3$ or —C$_2$F$_5$, q is an integer from 1 to 30;
said chains are obtained according to U.S. Pat. No. 4,523,039;

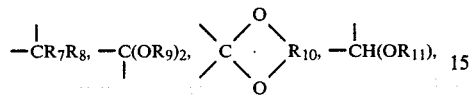

wherein R$_6$, R$_7$, R$_8$, R$_9$, R$_{11}$ are alkyl radicals containing from 1 to 3 carbon atoms, R$_6$, R$_7$ and R$_8$ can be also hydrogen; R$_{10}$ is an alkylene radical of from 1 to 3 carbon atoms;

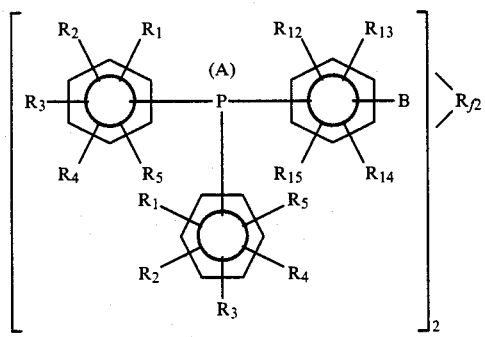

wherein R$_1$, R$_2$, R$_3$, R$_4$, R$_5$ and R$_{12}$, R$_{13}$, R$_{14}$, R$_{15}$, equal to or different from each other, can be —H, —F, —CF$_3$, —B—R$_{f1}$;
A, B, R$_{f1}$ have the above exposed meaning;
R$_{f2}$ is:

(d) —CF$_2$O(C$_2$F$_4$O)$_p$(CF$_2$O)$_q$—CF$_2$—,
wherein p and q are integers different from zero, and the p/q ratio ranges from 0.5 to 2, preferably from 0.5 to 1.5, the average molecular weight being comprised within the range of from 300 to 7000; said chains are obtained according to U.S. Pat. No. 3,715,378;

(e) 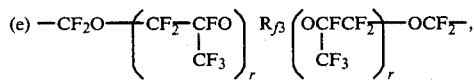

wherein r is an integer from 1 to 20 and R$_{f3}$ is a perfluoroalkylenic radical;
said chains are obtained according to EP Appln. No. 151,877;

(f) —CF$_2$O—(CF$_2$CF$_2$CH$_2$O)$_t$R$_{f3}$(OCH$_2$CF$_2$CF$_2$—)$_t$—OCF$_2$—,
wherein R$_{f3}$ has the meaning described hereinabove and t is an integer from 1 to 20;
said chains are obtained according to EP Appln. No. 148,482 and Italian Patent Application No. 22920 A/85;

(g) —CF$_2$O—(—CF$_2$CF$_2$CF$_2$O)$_s$—CF$_2$—,
wherein s has the meaning described hereinabove; said chains are obtained according to U.S. Pat. No. 4,523,039 and Italian Patent Application No. 22920 A/85.

(h) —CF$_2$O—(—CF$_2$CF$_2$O—)$_s$—CF$_2$—
wherein s has the meaning described hereinabove;
said chains are obtained according to U.S. Pat. No. 4,523,039 and Italian Patent Application No. 22920 A/85.

The products according to the present invention can be obtained according to the process as hereunder disclosed for the various B groups.

(a) For

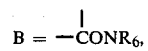

the process starts from phosphorus derivatives containing the —NHR$_6$ group, which are reacted with the phenyl ester of a perfluoroether acid, according to the following reaction scheme:

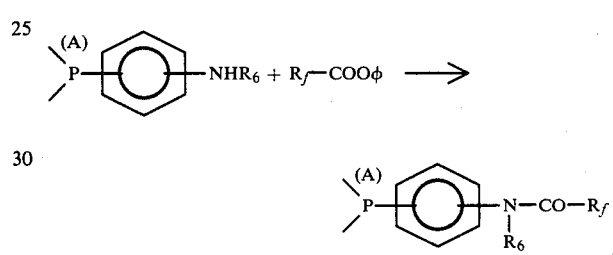

wherein R$_f$=R$_{f1}$ or R$_{f2}$, having the above indicated meaning.

(b) For B=—C(R$_7$)(R$_8$)O—, metal alkoxides having a perfluoroether chain are reacted with an aryl halide containing a mobile halogen. The reaction product is subsequently reacted with butyllithium and PCl$_3$ to obtain the phosphine.

(c) For B=—C(R$_7$)(R$_8$)OCH$_2$—, a metal alkoxide analogue to that described under (b) is condensed with a halomethyl-aryl derivative according to the following reaction scheme:

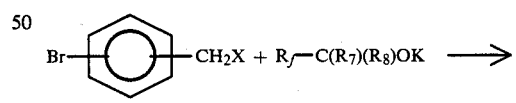

wherein
R$_f$=R$_{f1}$ or R$_{f2}$, having the above indicated meaning;
R$_7$ and R$_8$ have the above indicated meaning;
X=Cl, Br, I.

The subsequent known reactions with butyllithium and PCl$_3$ lead to the triarylphosphines of the invention.

(d) In case of B=—CH(OR$_{11}$), the process starts from a ketone having the following general formula:

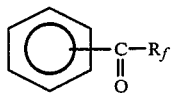

wherein $R_f = R_{f1}$ or $R_{f2}$, having the above indicated meaning.

The ketone is reduced by NaBH$_4$ to a secondary alcohol and is then alkylated, e.g., by alkyl sulphate. A halogenation on the ring is then carried out, followed by the known reactions with butyllithium and PCl$_3$ to obtain the phosphine.

(e) In case of

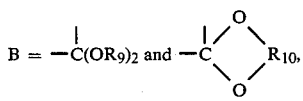

the process starts again from the same ketone as under (d); this is treated with an alcohol or a diol, a ketal is formed, by elimination of water. A halogenation on the ring, and then the known reactions with butyllithium and PCl$_3$ are carried out to obtain the phosphine.

(f) In order to obtain the group

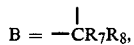

the process starts from the ketone described under (d). The carbonyl group is reduced, e.g., by hydrazine and/or an alkylated by means of, e.g., titanium derivatives; a halogenation on the ring and then the known reactions with butyllithium and PCl$_3$ are then carried out to obtain the phosphine.

The products of the invention are used as stabilizers for lubricating oils or greases having polyperfluoropolyether structure and are added to them in amounts comprised between 0.05 and 3.0% by weight, preferably between 0.5 and 1%.

The greases are obtained by adding a suitable thickener to the perfluoropolyether. This method for the preparation of greases is known in the art; it is disclosed, e.g., in published European Patent application EP 95,825.

The perfluoropolyethers used as lubricating oils or greases are selected from the hereinunder indicated classes of compounds comprising the constituting units of the following types:

(1) (C$_3$F$_6$O) and (CFXO) randomly distributed along the perfluoropolyether chain, wherein X is equal to —F, —CF$_3$;

(2) (C$_3$F$_6$O);

(3) (C$_3$F$_6$O), (C$_2$F$_4$O), (CFXO) randomly distributed along the perfluoropolyether chain, wherein X is equal to —F, —CF$_3$;

(4) (C$_2$F$_4$O), (CF$_2$O) randomly distributed along the perfluoropolyether chain;

(5) (CF$_2$CF$_2$CF$_2$O);

(6) (CF$_2$CF$_2$O).

The perfluoropolyethers which can be used with the products of the invention are selected in particular among those belonging to the following classes of perfluoropolyethers:

(1) CF$_3$O(C$_3$F$_6$O)$_m$(CFXO)Hd n—CF$_2$Y wherein Y can be —F or —CF$_3$ or —C$_2$F$_5$; X is equal to —F, —CF$_3$; m and n are integers and the m/n ratio ranges from 5 to 40.

These compounds are obtained by the process as disclosed in UK Pat. No. 1,104,482 and subsequent conversion of the end groups into chemically inert groups;

(2) C$_3$F$_7$O(C$_3$F$_6$O)$_m$—R$_f$ wherein R$_f$ can be —C$_2$F$_5$, —C$_3$F$_7$, —CFHCF$_3$ and m is a positive integer. These compounds are prepared according to U.S. Pat. No. 3,242,218;

(3) CF$_3$O(C$_3$F$_6$O)$_m$(C$_2$F$_4$O)$_n$(CFXO)$_q$—CF$_3$ wherein X is equal to —F, —CF$_3$; m, n and q are integers and the m/n+q ratio ranges from 0 to 50; n/q ranges from to 10.

These products are obtained by photooxidation of mixtures of C$_3$F$_6$ and C$_2$F$_4$ and subsequent treatment with fluorine according to the process as disclosed in U.S. Pat. No. 3,665,041;

(4) CF$_3$O(C$_2$F$_4$O)$_p$(CF$_2$O)$_q$—CF$_3$ wherein p and q are integers equal to or different from each other, the p/q ratio being comprised within the range of from 0.5 to 1.5. These perfluoropolyethers are prepared according to as disclosed in U.S. Pat. No. 3,715,378, being subsequently treated with fluorine according to U.S. Pat. No. 3,665,041;

(5) AO—(CF$_2$CF$_2$CF$_2$O)$_m$—A', wherein A and A', equal to or different from each other, can be —CF$_3$, 'C$_2$F$_5$, —C$_3$F$_7$, and m is an integer.

These products are obtained according to European Patent Application EP No. 148,482;

(6) DO—(CF$_2$CF$_2$O)$_r$—D', wherein D and D', equal to or different from each other, can be —CF$_3$, —C$_2$F$_5$, and r is an integer.

These products are obtained according to U.S. Pat. No. 4,523,039.

The result of the invention is much more surprising, in that it was totally unexpected that the replacement of —CF$_2$— bridge, obtained from the fluorination of C=O group, with a non-perfluorinated group would allow arylphosphines to be obtained with stability characteristics as high as those of the phosphines of the prior art under similar use conditions.

As a consequence, the products of the invention can be used, similarly to those of the prior art, as stabilizers of lubricating fluids or greases with perfluoropolyether structure in the process of metals at high temperatures and under an oxidizing atmosphere. Moreover, the products of the invention are soluble in the lubricant at the concentrations as indicated, without modifying the physical characteristics thereof, such as the lubricating power and the viscosity.

To the purpose of illustrating the invention, the following Examples are given, which are intended however as being not limitative of the same invention.

EXAMPLE 1

In a three-neck flask, 217 g of the product having the following formula:

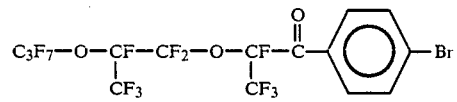

is added over a 1 hour time to a solution of NaBH$_4$ (19 g) in anhydrous ethyl alcohol (500 ml), maintaining the temperature at 15° 20° C. The reaction mass is kept under stirring for further 2 hours, and is then slowly hydrolyzed by 1000 ml of 1:1 HCl. The reaction mass is heated at 50° C. for 2 hours to complete the hydrolysis and the reaction product (lower phase) is separated and used in the subsequent step without further purification.

The yield of the described reaction is quantitative.

The so-obtained alcohol in slowly charged into a flask containing 70.6 g of 50% NaOH, 0.7 g of tetrabutylammonium chloride and 100 ml of ethyl ether. 57.5 g of dimethyl sulphate is slowly added under stirring, with the temperature being maintained at 40° C., the stirring is continued for 2 hours at 40° C., and the reaction mass is then diluted with $H_2O$. The organic phase is separated, washed with water, dried over sodium sulphate and the solvent is evaporated off.

By vacuum distillation of the reaction product, the methyl ether of formula:

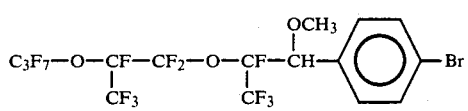

is obtained.

The reaction yield is of 90%.

To a solution of the so-obtained methyl ether in 2000 ml of a mixture of 40/60 diethyl ether/tetrahydrofuran cooled to −78° C., 193 ml of butyllithium (1.6M solution in hexane) is slowly added. After a 2 hours stirring of the reaction mixture, always at −78° C., a solution of 9.5 g of $PCl_3$ in diethyl ether is added. The temperature is raised up to −30° C. in a three hours time and the reaction mass is hydrolyzed by 200 ml of 6N HCl. The reaction mass is brought to room temperature, the ether phase is separated, washed with water, dried, and the solvent is evaporated off.

The arylphosphine, obtained as residual thick liquid at 150° C./0.5 $mm_{Hg}$, has the following formula:

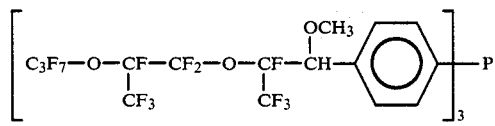

The structure of the arylphosphine is confirmed by infrared (I.R.) and NMR spectroscopic analyses ($^1H$ and $^{19}F$).

EXAMPLE 2

To a solution of potassium tert.butoxide (12.4 g=0.11 mol) in tert.butanol (150 ml) heated at 40° C., 64.8 g (0.1 mol) of

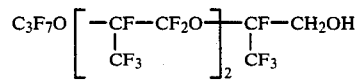

is added.

After stirring for 1 hour at 40° C., 24.7 g (0.1 mol) of bromopentafluorobenzene is added, and the mixture is refluxed for 2 hours. Tert.butyl alcohol is distilled off, the reaction mixture is diluted with $H_2O$ and with 1,1,2-trichloro-1,2,2-trifluoroethane solvent, and the organic phase is separated. After extraction of the aqueous phase with the same solvent, and combining of the organic phases, the solvent is evaporated off. By vacuum distillation of the reaction product, the brominated product of formula:

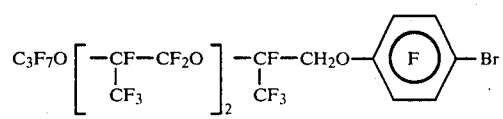

is obtained with yield 85%.

Such bromoderivative is converted into the corresponding phosphine by the process as disclosed in Example 1.

The following product is obtained:

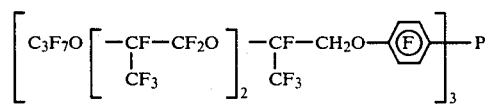

whose structure is confirmed by I.R. and N.M.R. of $^{19}F$ analyses.

EXAMPLE 3

45 g of a mixture of alcohols of general formula:

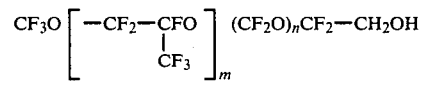

of average molecular weight 1050 with m/n ratio=4.3 is added to 5.28 g of potassium tert.butoxide in 500 ml of tert.butyl alcohol.

After a 2 hours stirring at 40° C., 12.9 g of 1-trifluoromethyl-3-chloromethyl-4-bromobenzene is added dropwise.

The reaction mass is refluxed for 4 hours.

KCl is filtered off, the solution of tert.butyl alcohol is separated as light phase, the product is washed with water after the addition of 1.1.2-trichloro-1,2,2-trifluoroethane to facilitate the separation of the phases.

The desired product is obtained with practically quantitative yields as the residual liquid after having evaporated off the solvent.

The results of I.R. and N.M.R. $^1H$- and $^{19}F$ analyses are in accordance with the formula

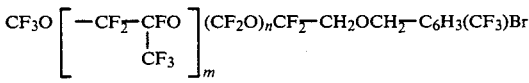

From the bromoderivate the corresponding phosphine is obtained by using the technique as described in Example 1.

EXAMPLE 4

370 g of triphenylphosphinoxide is portionwise added to a nitric acid/sulphuric acid mixture composed by 8.3 mol of $HNO_3$ and 18.4 mol of 98% sulphuric acid, with the temperature being maintained at 10°–15° C. The mixture is further stirred for ½ hour after the addition of the last portion, and the whole is poured into 7.5 liters of water and ice.

The precipitate is filtered off, washed with water and ice-cool ethanol.

The product is dried in oven at 110° C., and is then dissolved in acetic acid and precipitated by an excess of ethanol; it has melting point 241°-242° C., as measured by differential thermal analysis.

The I.R., N.M.R. and elemental analysis confirm the product to be substituted with nitro groups on the three phenyl rings in meta position, i.e., to be tris-(m-nitrophenyl)phosphinoxide.

200 g of tris-(m-nitrophenyl)phosphinoxide is portionwise added to a solution, kept under stirring at 90°-95° C. and constituted by 200 ml of water, 1200 ml of 36% hydrochloric acid and 1050 g of $SnCl_2$. After a further hour of stirring at 90°-95° C., at the end of the last addition of the nitroderivative, the reaction mixture is cooled and poured into an alkaline solution containing 3.9 mol of NaOH.

The precipitate is filtered off, washed with water and dissolved again in diluted sulphuric acid. The solution is decolorized by activated charcoal and is precipitated again with aqueous NaOH.

The precipitate, washed with water, is crystallized from methanol; its melting point is 256° C.

The titration with perchloric acid in acetic acid confirms the value of molecular weight to be 323, pertaining to tris-(m-aminophenyl)-phosphinoxide.

A portion of 60 g of tris-(m-aminophenyl)-phosphinoxide is added to 36.7 g of methylpolysiloxane and to 350 ml of diphenylether and is refluxed for 6 hours.

After cooling, 48 g crystallize (yield about 80%) of product having a melting point of about 200° C., which the analysis confirms to be tris-(m-aminophenyl)phosphine.

32.3 g of a mixture of phenyl esters of general formula

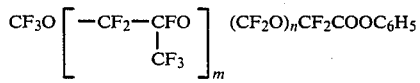

with m/n=4.1 and average molecular weight 1175 is reacted, under $N_2$ at 120°-140° C., with 2.81 g of tris(m-aminophenyl)-phosphine. The mixture turns clear, while phenol starts sublimating on the walls of the reaction flask. The heating at 140° C. is continued up to the complete removal of phenol.

A liquid product is discharged, which on I.R. analysis does not show any longer the absorption peak due to the ester CO (5.55μ), but shows the amidic peak (5.7-5.8μ) and hence corresponds to the formula:

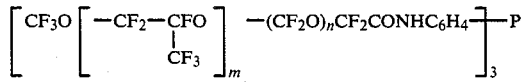

EXAMPLE 5

64.6 g of a mixture of phenyl esters, as of Example 4, of formula:

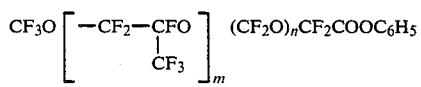

having average molecular weight 1175 is reacted at 120°-140° C. under $N_2$ atmosphere with the tris-(m-aminophenyl)phosphinoxide, prepared in the former Example.

After two hours, the reaction vessel is connected to the vacuum of a mechanical pump to distill off all the phenol evolving from the reaction.

A liquid product remains as the residue, which on I.R. analysis does not show any longer the absorption peak relating to the CO group of ester type, and has the formula:

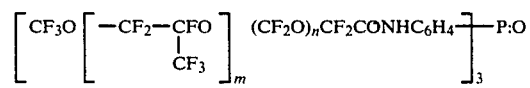

EXAMPLE 6

A series of tests is carried out to verify the thermooxidative stability in the presence of metals of lubricating compositions containing the stabilizers of the invention.

The equipment for such tests is constituted by a glass test tube equipped with a gas inlet pipe, with vent outlet and with means to house two metal discs, respectively of steel (AISI 304: 18 Cr, 10 Ni) and of Ti, V(4%), Al (6%) alloy.

Into the test tube, 50 g of perfluoropolyether fluid, covering the two metal discs, is introduced.

The test tube is heated to the desired temperature inside an aluminium oven.

Dry and pure air is bubbled through the perfluoropolyether fluid, at a flow rate od 1 l/h, for a time of 24 h. The tests are carried out at the temperatures of 288° and 316° C. respectively.

The lubricating compositions have been formulated by mixing a perfluoropolyether having the general formula:

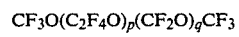

with a p/q ratio=0.8 and a kinematic viscosity of 285 cSt (at 20° C.) with the arylphosphines prepared in the foregoing Examples.

Also a comparison test has been carried out, wherein the polyperfluoroether does not contain any stabilizers.

The data obtained are reported in Table 1.

TABLE 1

| STABIL-IZER | % (*) | 288° C. ΔP % () | 288° C. % Δη20° C. (*) | 316° C. ΔP % () | 316° C. % Δη20° C. (*) |
|---|---|---|---|---|---|
| None | — | −52.1 | −89.8 | −100 | — |
| Example 1 | 1 | −0.23 | +0.84 | −3.4 | +3 |
| Example 2 | 1 | −1.31 | +1.6 | −3 | +1.7 |
| Example 3 | 1 | −1.5 | −2.5 | — | — |
| Example 4 | 1 | −0.7 | +5 | −2.3 | +2.8 |
| Example 5 | 1 | −0.9 | +4 | −1.85 | +2.85 |

(*)% by weight of stabilizer added;
(**)% change of lubricant weight;
(***)% change of lubricant viscosity.

We claim:
1. An arylphosphine selected from the group consisting of arylphosphines of the formula:

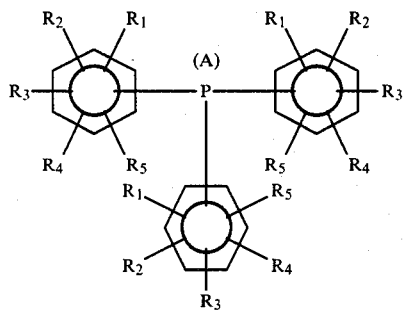

wherein A, when present, can be either oxygen or sulphur; $R_1, R_2, R_3, R_4, R_5$, equal to, or different from each other, are —H, —F, —CF$_3$ or —B—R$_{f1}$; with the constraint that at least one of the $R_1$-$R_5$ groups on at least one of benzene rings is a —B—R$_{f1}$ radical, wherein R$_{f1}$ is:

(a) Z—CF$_2$O(C$_3$F$_6$O)$_m$(CFXO)$_n$—CFY—, wherein
X=—F or —CF$_3$;
Y=—F or —CF$_3$;
Z=—F, —CF$_3$ or —CF$_2$—CF$_3$; in the latter case n=0 and Y=—CF$_3$;
m and n are integers, with m being comprised between 1 and 30 and n being comprised between 0 and 10, and the molecular weight of R$_{f1}$ is comprised within the range of from 135 to 6500 and the (C$_3$F$_6$O) and (CFXO) units are randomly distributed along the chain;

(b) X—(CF$_2$CF$_2$CW$_2$O)$_p$—
wherein Z has the meaning described above, W is H or F and p is an integer from 1 to 30; or (c) D—(CF$_2$CF$_2$O)$_q$— wherein d is —CF$_3$ or —C$_2$F$_5$, q is an integer from 1 to 30;

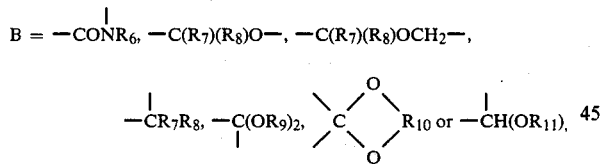

wherein $R_6, R_7, R_8, R_9$ and $R_{11}$ are alkyl radicals containing from 1 to 3 carbon atoms, $R_6, R_7$ and $R_8$ can be also hydrogen; $R_{10}$ is an alkylene radical of from 1 to 3 carbon atoms; and

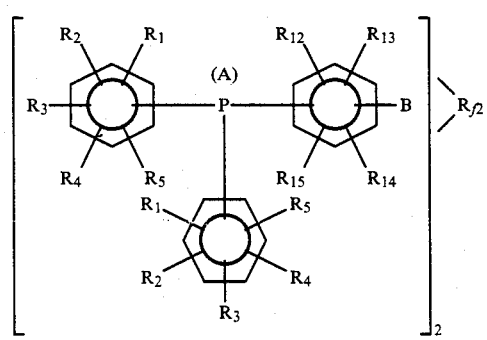

wherein $R_1, R_2, R_3, R_4, R_5, R_{12}, R_{13}, R_{14}$ and $R_{15}$, equal to or different from each other are —H, —F, —CF$_3$ or —B—R$_{f1}$;
A, B, R$_{f1}$ have the same meaning as above;
R$_{f2}$ is:

(d) —CF$_2$O(C$_2$F$_4$O)$_p$(CF$_2$O)$_q$—CF$_2$—;
wherein p and q are integers different from zero, and the p/q ratio ranges from 0.5 to 2, preferably from 0.5 to 1.5, the average molecular weight being comprised within the range of from 300 to 7000;

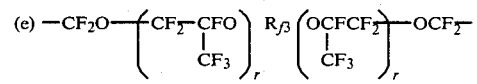

wherein r is an integer from 1 to 20 and R$_{f3}$ is a perfluoroalkylenic radical;

(f) —CF$_2$O—(CF$_2$CF$_2$CF$_2$O)$_t$R$_{f3}$(OCH$_2$CF$_2$CF$_2$)$_t$—OCF$_2$—,
wherein R$_{f3}$ has the meaning described hereinabove and t is an integer from 1 to 20;

(g) —CF$_2$O—(—CF$_2$CF$_2$CF$_2$O—)$_s$CF$_2$—,
wherein s is an integer from 1 to 30; or (h) —CF$_2$O—(—CF$_2$CF$_2$O—)$_s$—CF$_2$—,
wherein s has the meaning described herein above.

2. An arylphosphine according to claim 1, of the formula:

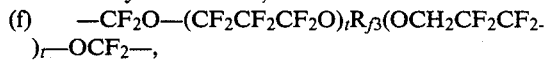

3. An arylphosphine according to claim 1, of formula:

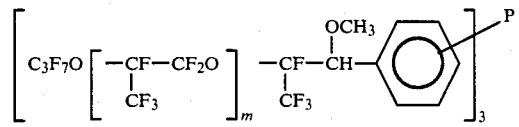

4. An arylphosphine according to claim 1, of formula:

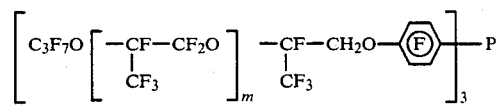

5. An arylphosphine according to claim 1, of formula:

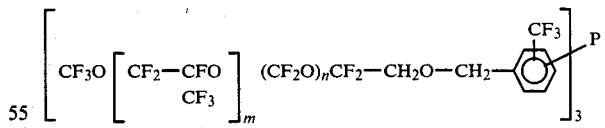

6. An arylphosphine according to claim 1, of the formula:

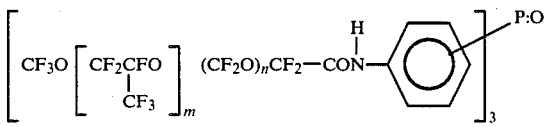

7. A lubricating composition comprising a perfluoropolyether oil or grease and 0.05-3% by weight of an arylphoshine according to claim 1.

8. A lubricating composition according to claim 7, wherein the perfluoropolyether oil or grease has a structural unit or units selected from the group consisting of:
(1) $(C_3F_6O)$ and $(CFXO)$ randomly distributed along the perfluoropolyether chain, wherein X is equal to —F or —$CF_3$;
(2) $(C_3F_6O)$;
(3) $(C_3F_6O)$, $(C_2F_4O)$, $(CFXO)$ randomly distributed along the perfluoropolyether chain, wherein X is equal to —F or —$CF_3$;
(4) $(C_2F_4O)$ and $(CF_2O)$ randomly distributed along the perfluoropolyether chain;
(5) $(CF_2CF_2CF_2O)$; and
(6) $(CF_2CF_2O)$.

9. A lubricating composition according to claim 7, wherein the polyfluoropolyether oil or grease is selected from the group consisting of:
(1) $CF_3O(C_3F_6O)_m(CFXO)_n$—$CF_2Y$
wherein Y can be —F, —$CF_3$ or —$C_2F_5$; X is equal to —F or —$CF_3$; m and n are integers and the m/n ratio ranges from 5 to 40;
(2) $C_3F_7O(C_3F_6O)_m$—$R_f$
wherein $R_f$ can be —$C_2F_5$, —$C_3F_7$ or —$CFHCF_3$ and m is a positive integer;
(3) $CF_3O(C_3F_6O)_m(C_2F_4O)_n(CFXO)_q$—$CF_3$ wherein X is equal to —F or —$CF_3$; m, n and q are integers and the m/n+q ratio ranges from 0 to 50, n/q ranges from 0 to 10;
(4) $CF_3O(C_2F_4O)_p(CF_2O)_q$—$CF_3$
wherein p and q are integers equal to or different from each other, the p/q ratio being comprised within the range of from 0.5 to 1.5;
(5) $AO$—$(CF_2CF_2CF_2O)_m$—$A'$,
wherein A and A' equal to or different from each other, can be —$CF_3$, —$C_2F_5$ or —$C_3F_7$, and m is an integer; and
(6) $DO$—$(CF_2CF_2O)_r$—$D'$,
wherein D and D' equal to or different from each other, can be —$CF_3$ or —$C_2F_5$, and r is an integer.

10. A lubricating composition according to claim 7, comprising 0.5 to 1% by weight of the arylphosphine.

* * * * *

UNITED STATES PATENT AND TRADEMARK OFFICE
CERTIFICATE OF CORRECTION

PATENT NO. : 4,681 693

DATED : July 21, 1987

INVENTOR(S) : Piero GAVEZOTTI and Ezio STREPPAROLA

It is certified that error appears in the above-identified patent and that said Letters Patent is hereby corrected as shown below:

Column 14, line 20: in the structural formula for (f), for the fourth occurrence of "$F_2$" in that line read --$H_2$--

Signed and Sealed this

Twenty-ninth Day of May, 1990

Attest:

HARRY F. MANBECK, JR.

Attesting Officer     Commissioner of Patents and Trademarks